United States Patent
Cerwin et al.

[11] Patent Number: 5,918,733
[45] Date of Patent: Jul. 6, 1999

[54] LIGATING REEL PACKAGE

[75] Inventors: Robert J. Cerwin, Pipersvile, Pa.; Deborah M. Transue, Bridgewater, N.J.

[73] Assignee: Ethicon, Inc., Somerville, N.J.

[21] Appl. No.: 09/057,256

[22] Filed: Apr. 8, 1998

[51] Int. Cl.[6] .......................... A61B 17/06; B65D 73/00
[52] U.S. Cl. .......................................... 206/63.3; 206/486
[58] Field of Search ................................. 206/63.3, 380, 206/227, 486, 487, 488, 489, 490, 418, 419, 422, 408

[56] References Cited

U.S. PATENT DOCUMENTS

| | | | |
|---|---|---|---|
| 2,015,222 | 9/1935 | Hinson | 206/418 |
| 3,462,020 | 8/1969 | Hall | 206/419 |
| 4,572,362 | 2/1986 | Kronfeld | 206/418 |
| 4,763,786 | 8/1988 | Benz | 206/408 |
| 5,460,263 | 10/1995 | Brown et al. | |

FOREIGN PATENT DOCUMENTS 0611180  10/1948  United Kingdom ................... 206/418

*Primary Examiner*—Paul T. Sewell
*Assistant Examiner*—J. Mohandesi
*Attorney, Agent, or Firm*—Emil Richard Skula

[57] ABSTRACT

A package for a surgical suture reel. The package has a substantially flat base member with a mounting tab formed therein by an arcuate slit. The mounting tab has a central opening and a plurality of radial slits surrounding the opening forming engagement members.

9 Claims, 5 Drawing Sheets

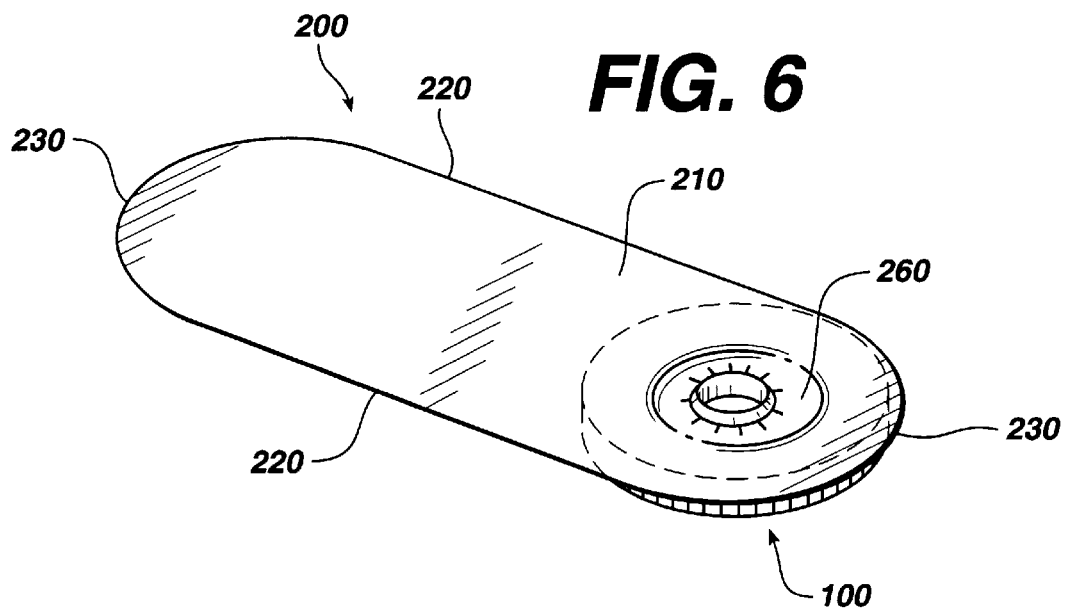
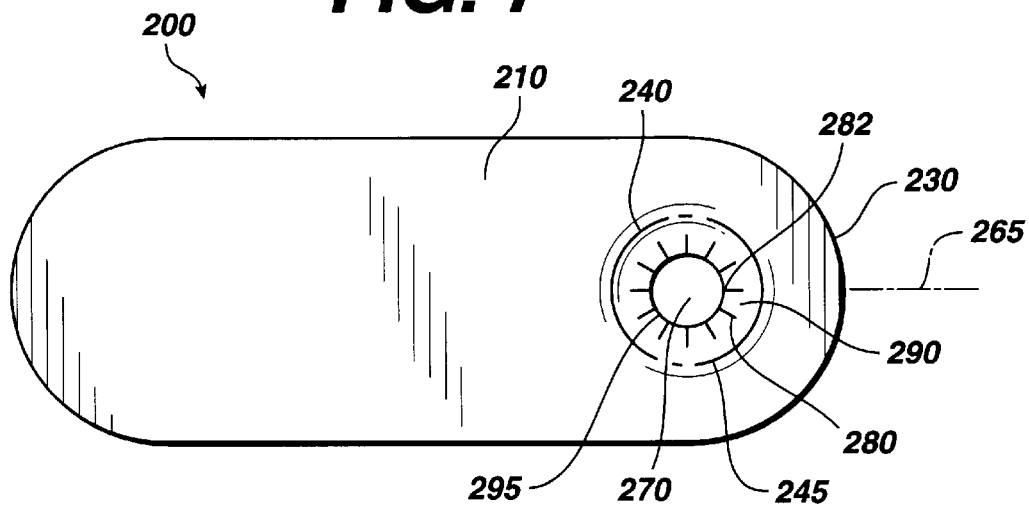

LIGATING REEL PACKAGE

TECHNICAL FIELD

The field of art to which this invention relates is packaging, in particular, packaging for surgical sutures.

BACKGROUND OF THE INVENTION

Packages for surgical sutures are well known in the art. The packages may be conventional folder packages made from paperboard, or conventional molded or formed plastic packages having suture retaining channels. The packages must retain and protect the surgical needles during sterilization, shipping, handling, and storage. In addition, the sutures must be easily removable from the package by the surgeon or the surgeon's assistant.

Typically, most surgical sutures are sold having surgical needles mounted to one or both ends of the suture. Such surgical needle suture combinations are mounted or packaged in the above-described packages. However, for certain surgical procedures, such as the ligation of blood vessels, it is preferred to utilize surgical sutures which do not have surgical needles mounted to the ends thereof. Such sutures are conventionally mounted in packages known as ligating reels. These ligating reels typically have a reel member having a central opening, and a cover member having a central hub. Suture is wound onto the reel which is then rotatably mounted to the hub of the cover. Suture is removed from the reel by holding the cover while grasping and pulling a free suture end, thereby causing the reel to rotate as the suture is withdrawn. Typically, the lengths of the sutures packaged in ligating reels are longer than those packaged in other types of conventional suture packages. There are several reasons for packaging sutures in ligating reel packages, including ease of use when the surgeon is holding a reel during manual knot tying, and the ability to pull varying lengths of suture from the reel while knot tying.

As mentioned above, a conventional ligating reel package typically consists of a rotatable reel structure having a central opening. The reel is rotatably mounted to a cover member having a hub extending therefrom. The cover member houses the reel and protects the suture which has been previously mounted or wound onto the reel. The reel package may optionally be wrapped in desiccant paper, depending upon the moisture sensitivity of the suture material. The reel is then mounted in a conventional outer package and sterilized using a conventional sterilization process such as gas sterilization, radiation, autoclaving and the like.

Although conventional ligating reels are effective for their intended use, there are certain disadvantages attendant therewith. For example, the reel in some instances may be difficult to remove from its outer package. And, subsequent to removal, the reel may be difficult to firmly grasp because of its circular configuration, particularly with a wet, gloved hand. In addition, most ligating reels are relatively small and, accordingly, are difficult to label. Typically, the exterior package is labeled but not the ligating reel itself. This may result in an undesirable situation wherein the ligating reel, when separated from the outer packaging, is unlabelled.

Accordingly, there is a need in this art for improved ligating reel packages which overcome these deficiencies.

SUMMARY OF THE INVENTION

Therefore, it is an object of the present invention to provide a novel ligating reel mounting base member to which a ligating reel may be easily mounted and which may be further packaged directly into a secondary package such as a peelable pouch.

It is a further object of the present invention to provide a mounting base member which can carry required labeling and which serves as a holder which the surgeon can grasp while withdrawing suture from the ligating reel.

It is yet a further object of the present invention to provide a novel ligating reel mounting base member which is useful in an automated packaging and mounting process and which has dimensional stability.

It is still yet a further object of the present invention to provide a novel ligating reel mounting base member which can be firmly attached to a reel thereby providing reliable transfer into a sterile field.

Yet another object of the present invention is a novel ligating reel mounting base which can serve as a desiccant paper for synthetic absorbable suture materials.

Accordingly, a surgical suture ligating reel package is disclosed. The package has a mounting base. The mounting base consists of an elongated flat base member having opposed first and second longitudinal sides, connected by opposed first and second ends, preferably rounded. The base member has a longitudinal axis. Adjacent to one rounded end is an arcuate slit forming a mounting tab. The mounting tab is preferably positioned along the longitudinal axis. Intersecting the arcuate slit at one end are a pair of opposed, parallel longitudinal hinge slits forming a hinge tab such that the mounting tab is rotatable about the hinge tab. Centrally located through the mounting tab is the hub mounting hole. The hub mounting hole is surrounded by a plurality of radial slits extending partially into the mounting tab, forming a plurality of engagement fingers.

Yet another aspect of the present invention is a ligating reel package assembly. The assembly consists of a mounting base and a ligating reel package. The mounting base consists of an elongated flat base member having opposed first and second longitudinal sides, connected by opposed first and second opposed rounded ends. The base member has a longitudinal axis. Adjacent to one rounded end is an arcuate slit forming a hub mounting tab. The mounting tab is located along the longitudinal axis. Intersecting the arcuate slit at one end are a pair of longitudinal, opposed parallel hinge slits forming a hinge tab such that the mounting tab is rotatable about the hinge tab. Centrally contained located through tab is the hub mounting hole. The mounting hole is surrounded by a plurality of radial slits extending partially into the mounting tab, the radial slits forming a plurality of engagement fingers. Mounted in the mounting hole of the mounting tab is an end of a hub of a ligating reel package. The ligating reel package has a suture reel member having a circular central disk with a circumferential rim. The rim has an outer surface and opposed sides. The disk has a central opening for receiving a hub. A plurality of opposed containment members extend radially outward from the sides of the rim to form an annular cavity for receiving suture material. A cover member, with an exterior and an interior, and having a central hub extending outwardly from the interior is mounted to the reel, such that the hub extends through the cylindrical member, thereby allowing the reel to rotate upon the hub. The hub has an end. The end of the hub is mounted in the hub mounting hole of the mounting member, and is retained by the engagement fingers.

Still yet another aspect of the present invention is a ligating reel package as described above, but having a mounting tab that is not hinged.

Another aspect of the present invention is a ligating reel package as described above, but having a mounting opening without a mounting tab.

These and other aspects of the present invention will become more apparent from the following description and accompanying drawings.

BRIEF DESCRIPTION OF THE DRAWINGS

FIG. 6 is a perspective view of an alternate embodiment of a ligating reel mounting package of the present invention which does not rave a hinged mounting tab.

FIG. 7 is a top view of the mounting package base member of FIG. 6.

DESCRIPTION OF THE PREFERRED EMBODIMENTS

Figure 1:
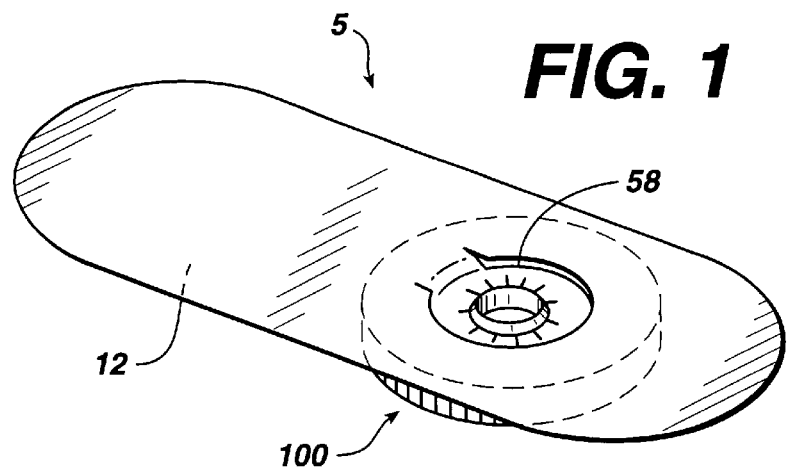
FIG. 1 is a perspective view of a ligating reel mounting package of the present invention having a ligating reel mounted thereto.
Figure 2:
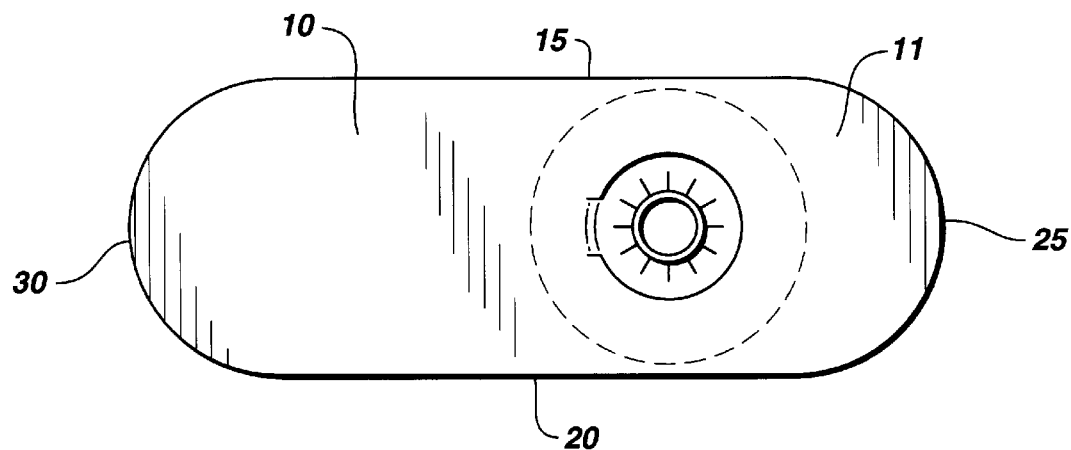
FIG. 2 is a bottom view of the package of FIG. 1 showing the ligating reel in phantom.
Figure 3:
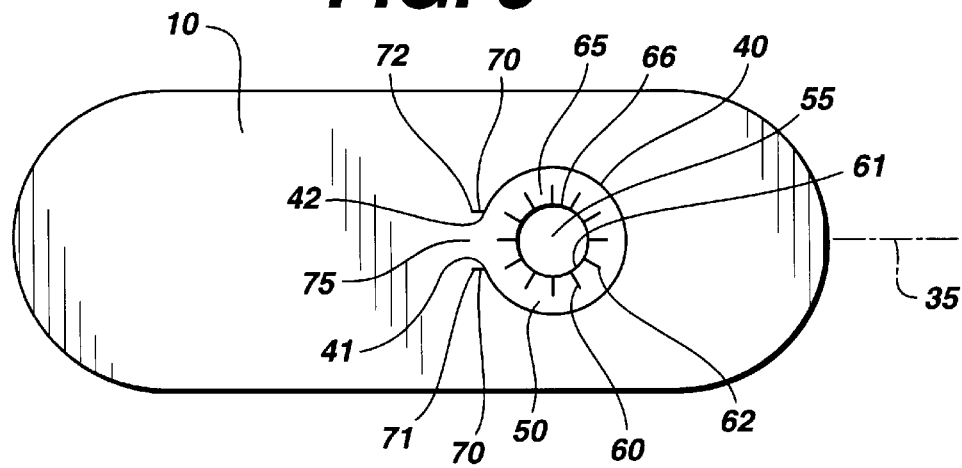
FIG. 3 is a top view of the package of FIG. 1.

Referring to FIG. 1, a perspective view of a ligating reel mounting package of the present invention is illustrated. The package 5 is seen to be assembled having a conventional surgical suture ligating reel 100 mounted thereto. As further illustrated in FIGS. 2–5, the ligating reel package 5 of the present invention is seen to have a substantially flat base member 10. Base member 10 is seen to have a pair of opposed, substantially parallel sides 15 and 20 connected by opposed rounded ends 25 and 30. Ends 25 and 30 may have other configurations including straight, triangular, polygonal, etc. Base member 10 is also seen to have longitudinal axis 35. The base member 10 is seen to have top side 11 and bottom side 12. Base member 10 is also seen to have arcuate slit 40, having ends 41 and 42, forming mounting tab 50. Mounting tab 50 is seen to have central opening 55. Central opening 50 is preferably circular, but may have other equivalent configurations. Mounting tab 50 is preferably located along longitudinal axis 35, although it may be located anywhere within base member 10. Surrounding opening 55 are a plurality of radial slits 60 having one end 61 extending through to opening 55 and opposed end 62. Slits 60 are seen to form engagement or mounting fingers 65 having ends 66. Ends 66 may be flat or curved. Base member 10 is also seen to have opposed parallel slits 70 having ends 71 and 72 forming hinge member 75. The ends 71 and 72 of slits 70 intersect the ends 41 and 42, respectively, of slit 40. Tab 50 is rotatable about hinge member 75 to form opening 58.

Figure 4:
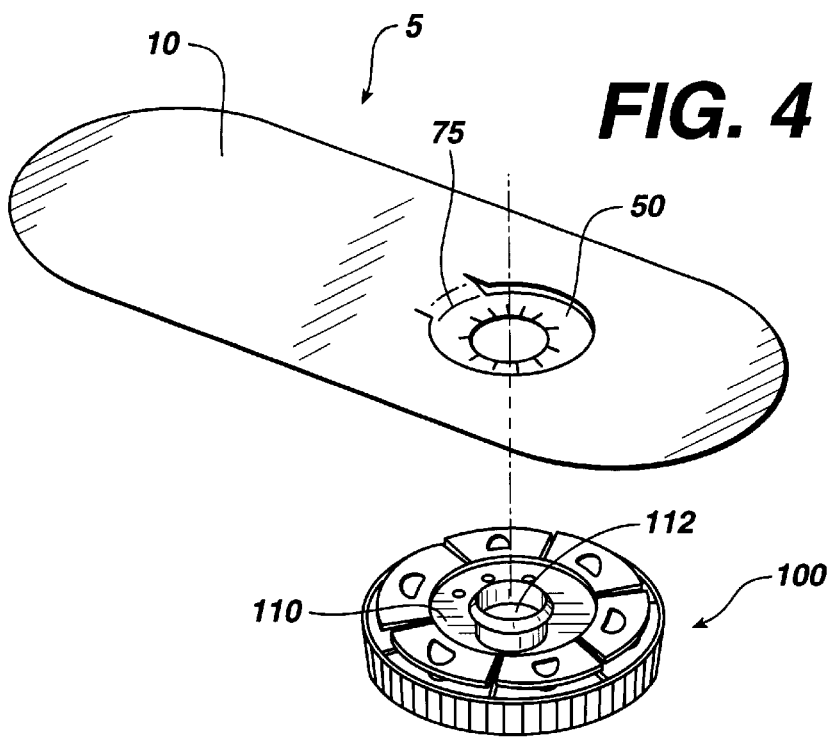
FIG. 4 is an exploded perspective view of a ligating reel and a mounting package of the present invention.
Figure 5:
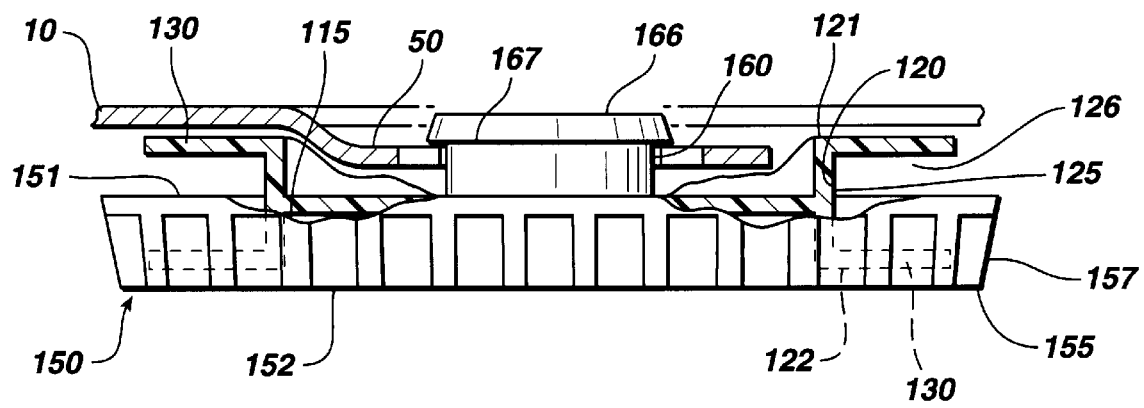
FIG. 5. is a partial cross-sectional view taken along View Line 5—5 of the ligating reel and package of FIG. 1 showing the hub of a ligating reel mounted in the mounting tab of the mounting package base member.

Referring to FIGS. 4 and 5, a conventional surgical suture reel assembly 100 is seen. Reel 100 is seen to have central spool member 110. Spool member 110 has a flat circular disc structure having outer circumference 115. Contained through the center of member 110 is central opening 112. Extending axially from spool member 110 about circumference 115 is circumferential rim member 120 having opposed sides 121 and 122 and circumferential exterior surface 125. Extending radially from sides 121 and 122 are the opposed reel member side flanges 130. Flanges 130 and surface 125 provide an annular channel 126 for winding a suture onto the spool member 110. The reel 100 is also seen to have cover member 150 having central hub member 160. Cover member 150 has inner side 151 and outer side 152. Cover member 150 is seen to be a flat disc-like circular member having a circumferential perimeter 155. Circumferential rim member 157 extends axially up from the inner side 151 about perimeter 155. Hub member 160 is seen to extend axially up from the center of the inner side 151 member 150 and to have free end 166 and optional retention flange 167 extending radially outward from end 166. Spool 110 is rotatably mounted to hub 160 of cover 150 by sliding spool 110 over hub 160 via opening 112 to form the assembled reel 100.

The package 5 is assembled in the following manner. Mounting tab 50 is pushed upward and rotates slightly about hinge member 75 such that the member 50 is raised slightly above the top surface 11 of member 10, thereby forming opening 58 in the member 10. Then the flange 167 extending radially outwardly from the end 166 of hub member 160 is pushed through opening 55 displacing the engagement members 65 downwardly to engage the optional flange member 167 and the ends 66 engage the exterior of the end 166 of hub 160, and thereby lock the reel 100 to the mounting tab 50 of base member 10 to form assembled package 5.

Referring to FIG. 6 and FIG. 7, an additional embodiment of a ligating reel mounting package of the present invention is seen. The package 200 is seen to have a substantially flat base member 210 having opposed longitudinal sides 220 and opposed curved ends 230 connecting the longitudinal sides 220. Located toward one end 230 of the base member 210 along the longitudinal axis 265, there is seen to be a hub mounting opening 270. Opening 270 is surrounded by plurality of radial slits 280 forming engagement members 290. Slits 280 have ends 282 in communication with opening 270. Engagement members 290 are seen to have ends 295. In addition, a pair of opposed discontinuous arcuate slits 240 and 245 are located concentrically about the mounting hole 270 and engagement members 290, forming mounting tab 260. A ligating reel 100 is mounted to base member by inserting the end 166 of hub member into opening 270 such that the ends 295 of engagement fingers 290 engage hub 160 and the engagement fingers 290 engage flange 167.

Figure 8:
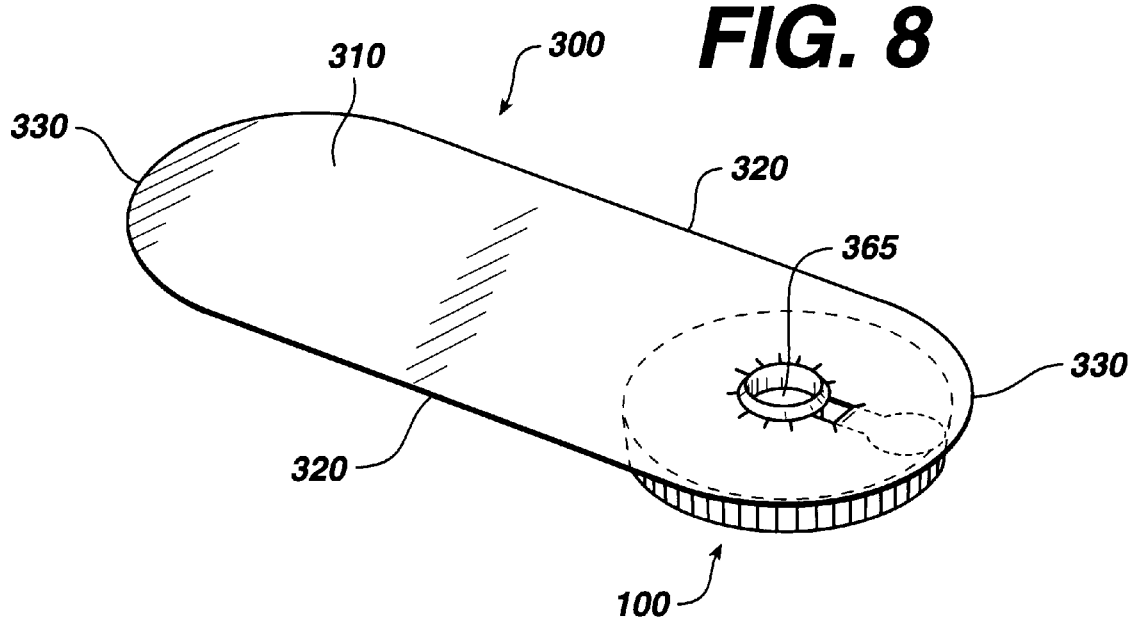
FIG. 8 is a perspective view of an additional embodiment of a ligating reel mounting package of the present invention.
Figure 9:
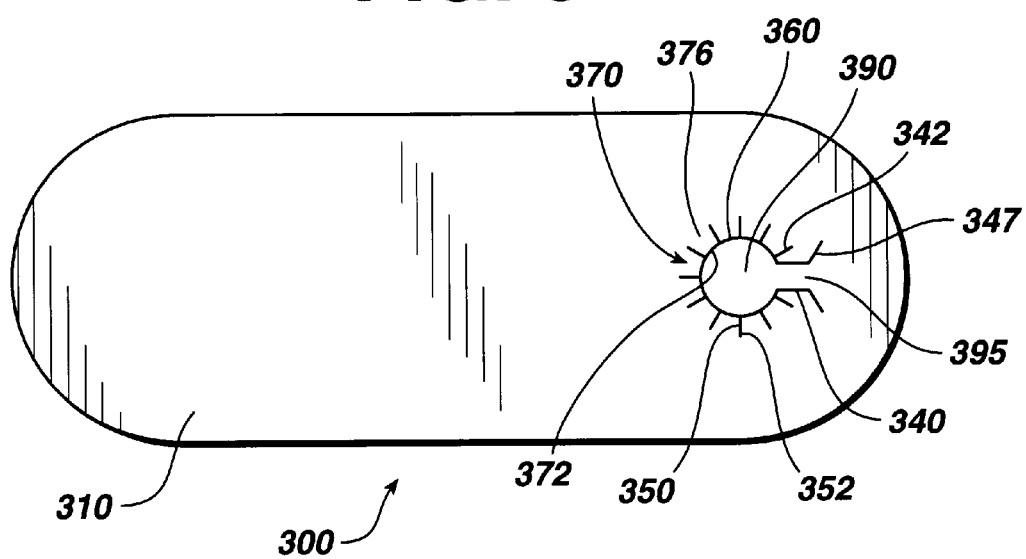
FIG. 9 is a top view of the mounting package base member of FIG. 8.

Yet another embodiment of a ligating reel mounting package of the present invention is seen in FIGS. 8 and 9. The package 300 is seen to have substantially flat base member 310 having opposed curved ends 330 connected by opposed parallel sides 320. Located toward one end of the base member 310 is seen the tab member 390. The tab member 390 is formed by arcuate slit 360, the opposed parallel longitudinal slits 340 which have ends 342 which intersect slit 360 and opposed angulated ends 347 forming tab member base 395. The tab member 390 is rotatable around the base 395 to form the opening 365. The opening 340 is seen to be surrounded by a plurality of radial slits 350 having ends 352 which intersect slit 340. The slits 350 are seen to form the hub engagement fingers 370 having free ends 372 and fixed ends 376. The hub 160 of a ligating reel package 100 is mounted into the hub receiving hole 365 of base member 310 such that the end 166 of the hub 160 is engaged by the ends 372 of hub engagement fingers 370 and any flange member 167 is also engaged by fingers 370.

Figure 10:
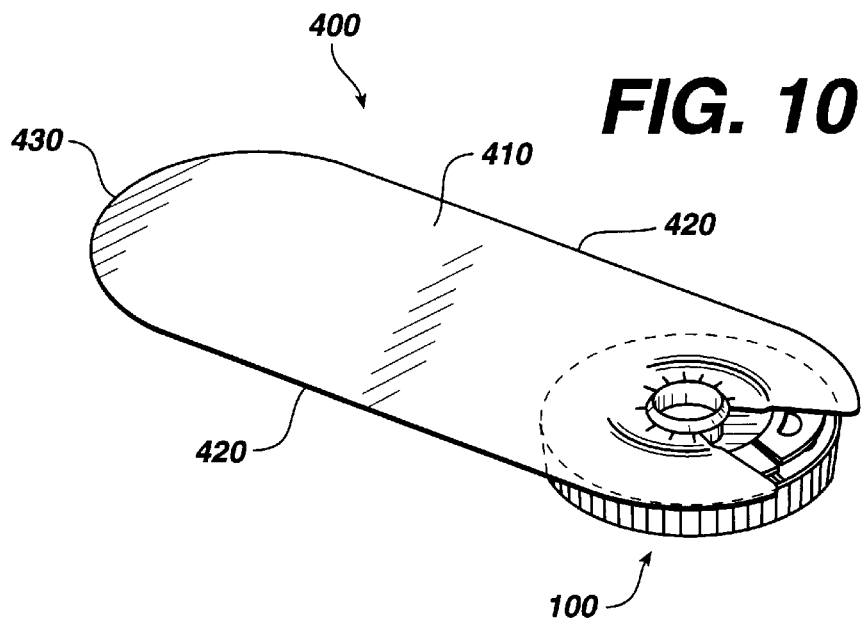
FIG. 10 is a perspective view of an additional embodiment of a ligating reel mounting package of the present invention.
Figure 11:
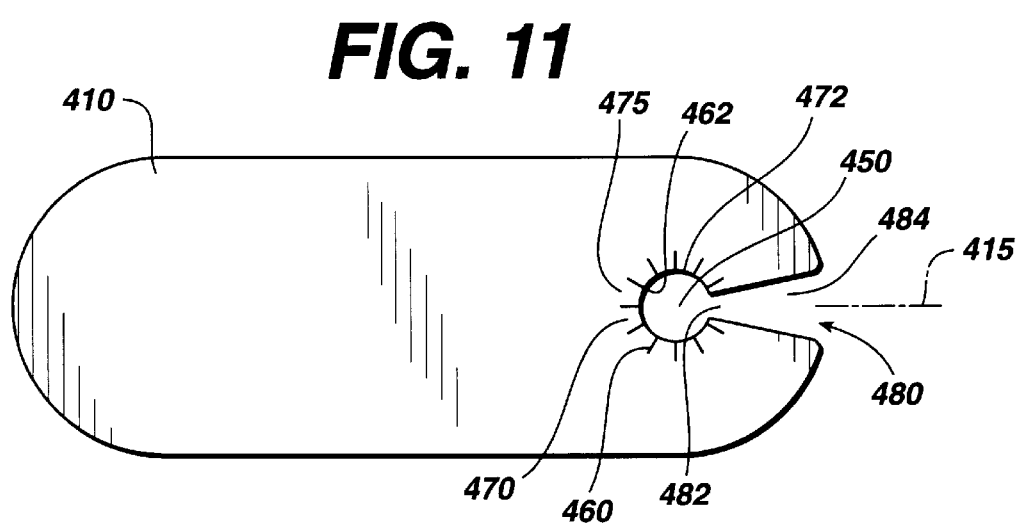
FIG. 11 is a top view of the mounting package base member of FIG. 10.

Yet another embodiment of a ligating reel mounting package of the present invention is illustrated, FIGS. 10 and 11. The package 400 is seen to have base member 410 having opposed rounded ends 430 connected by opposed parallel longitudinal sides 420. Toward one end 430 of the base member 410 is located the hub mounting hole 450. Hole 450 is seen to be aligned along longitudinal axis 415. A slot 480 is seen to be contained in base member 410 adjacent to the opening 450. Slot 480 is seen to have receiving mouth 484 and end 482 in communication with opening 450. The opening 450 is seen to be surrounded by a plurality of radial slots 460 having ends 462 which intersect opening 450. The slots 460 are seen to form hub engagement fingers 470 having free ends 472 and fixed ends 475. A reel package 100 is mounted to the package 400 by sliding the end 166 of the hub member 160 through the slot 480 into opening 450 such that the ends 472 of the engagement members 470 engage the surface of the end 166 of the hub 160 and the fingers 470 engage optional flange member 167.

The folder packages 5 of the present invention are preferably constructed from any material having the required structural characteristics such that the material can be readily die cut, and scored. In addition, the material must be easily folded and sterilizable. The materials include those known in the art for packaging sutures and medical devices, including medical grade papers, plastic, foils, and laminates of one or more thereof. However, it is particularly preferred in the practice of the present invention to utilize a heavyweight, relatively stiff, medical grade paper or paperboard such as, for example, 0.007–0.024" suture board. The base members of the packages of the present invention may act as a desiccant when constructed of conventional desiccant materials, for example, paperboard.

Typically, the packages of the present invention such as package 5 having suture reels 100 mounted thereto are packaged in conventional outer envelopes or packages prior to sterilization. Conventional envelopes useful as outer envelope 10 may be made from polymer films including TYVEK®, polyester copolymers, polypropylene copolymers, polyethylene copolymers, laminates and combinations thereof, and the like. The outer envelopes or packages may also be made from polymer film, paper, and foil combinations. The packages 5 are preferably packaged in a conventional moisture proof foil package, such as a foil envelope, when used for bioabsorbable sutures. As mentioned previously, the package 5 may function as a desiccant when constructed from the appropriate conventional materials. The outer envelopes preferably function as sterile barriers when conventionally sealed. The package 5 having reel 100 mounted thereto may be optionally sterilized using conventional sterilization processes, such as ethylene oxide sterilization, radiation sterilization and autoclaving.

In use, in the operating room setting, the suture package 5 having a suture reel mounted thereto is removed from an outer package or pouch and placed in the sterile field of the operating room. The surgeon may then grasp the package 5 by holding onto the base member 10 while removing suture from the suture reel 100. This allows the surgeon or the surgeon's assistant to positively engage and control the suture reel 100 via the package 5 while removing suture from the reel 100. In addition, the package 5 may contain labeling such that the surgeon would know what type of suture is contained on reel 100 after reel 100 is removed from the outer package.

The packages of the present invention have many advantages. They are easy to manufacture out of conventional materials. The packages are extremely easy to assemble. The packages of the present invention are economical to manufacture. Surprisingly and unexpectedly, the packages of the present invention provide a base member which does not bow when a ligating reel 100 is mounted to the base member. This allows for efficient assembly and for the use of a reduced thickness of the base member. In addition, the packages of the present invention provide for stability when used in automated packaging processes during which the packages may be vibrated. Other advantages include protection of the reel 100 from damage and shifting during shipping, handing and storage. When removed from an outer package, the surgeon may conveniently and positively grasp package 5 with a gloved hand while removing suture from a suture reel, greatly facilitating this procedure, even when the gloved hand is wet.

Although this invention has been shown and described in respect to detailed embodiments thereof, it will be understood by those skilled in the art the various changes in form and detail thereof may be made without departing from the spirit and scope of the claimed invention.

We claim:

1. A package for a surgical suture ligating reel comprising:
    an elongated substantially flat mounting base member, said member having a pair of opposed first and second longitudinal sides connected by first and second opposed ends;
    an arcuate slit in said base forming a mounting tab;
    a pair of opposed, parallel slits intersecting said actuate slit, forming a hinge member;
    a central opening in said mounting tab; and,
    a plurality of radial slits in said mounting member, said slits intersecting said opening, wherein said slits form engagement members, each member having a free end and a fixed end.

2. The package of claim 1 wherein the opposed ends are arcuate.

3. The package of claim 1 wherein the base member comprises a desiccant material.

4. A package for a surgical suture ligating reel comprising:
    an elongated substantially flat mounting base member, said member having a pair of opposed first and second longitudinal sides connected by first and second opposed ends;
    a pair of opposed arcuate slits in said base defining a mounting tab;
    a central opening in said mounting tab; and,
    a plurality of radial slits in said mounting member, said slits intersecting said opening, wherein said slits form engagement members, each member having a free end and a fixed end.

5. The package of claim 4 wherein the opposed ends are arcuate.

6. The package of claim 4 wherein the base member comprises a desiccant material.

7. A package for a surgical suture ligating reel comprising the combination of:
    A. a package for a surgical suture reel comprising:

an elongated substantially flat mounting base member, said member having a pair of opposed first and second longitudinal sides connected by first and second opposed ends;
an arcuate slit in said base forming a mounting tab;
a pair of opposed, parallel slits intersecting said actuate slit, forming a hinge member;
a central opening in said mounting tab; and,
a plurality of radial slits surrounding said opening and intersecting said opening, thereby forming engagement members, each engagement member having a fixed end and a free end; and B. a surgical suture reel comprising a reel rotatably mounted to a hub extending from a cover member, wherein at least part of the hub is mounted in the central opening of the mounting tab, and the hub is engaged by at least one end of at least one engagement member.

8. The package of claim 7 wherein the opposed ends are arcuate.

9. The package of claim 7 wherein the base member comprises a desiccant material.

* * * * *